United States Patent [19]

Rosen

[11] 4,378,854
[45] Apr. 5, 1983

[54] BLOOD COLLECTION BAG WEIGHING DEVICE

[75] Inventor: Evan W. Rosen, Tucson, Ariz.

[73] Assignee: Engineering & Research Associates, Inc., Tucson, Ariz.

[21] Appl. No.: 314,586

[22] Filed: Oct. 26, 1981

Related U.S. Application Data

[63] Continuation-in-part of Ser. No. 81,164, Oct. 2, 1979.

[51] Int. Cl.³ .................. G01G 13/02; G01G 3/08; G01G 23/00
[52] U.S. Cl. .................................. 177/118; 177/229; 177/245
[58] Field of Search .............. 177/116, 118, 229, 245

[56] References Cited

U.S. PATENT DOCUMENTS 3,698,494 10/1972 Gaudin ............................ 177/245 X
3,924,700 12/1975 Lindsey et al. .................... 177/118
4,027,735 6/1977 Floyd .............................. 177/229 X Primary Examiner—George H. Miller, Jr.
Attorney, Agent, or Firm—Cahill, Sutton & Thomas

[57] ABSTRACT

A blood collection bag is suspended from a leaf spring, which leaf spring, on being repositioned a specified distance by the weight of a properly filled blood collection bag, energizes an electrical circuit. The electrical circuit generates a pulse to momentarily energize a coil in proximity to a permanent magnet and momentarily disrupt the magnetic field of the magnet. A clamp for terminating the flow of blood to the blood collection bag is actuated upon the disruption of the magnetic field.

8 Claims, 9 Drawing Figures

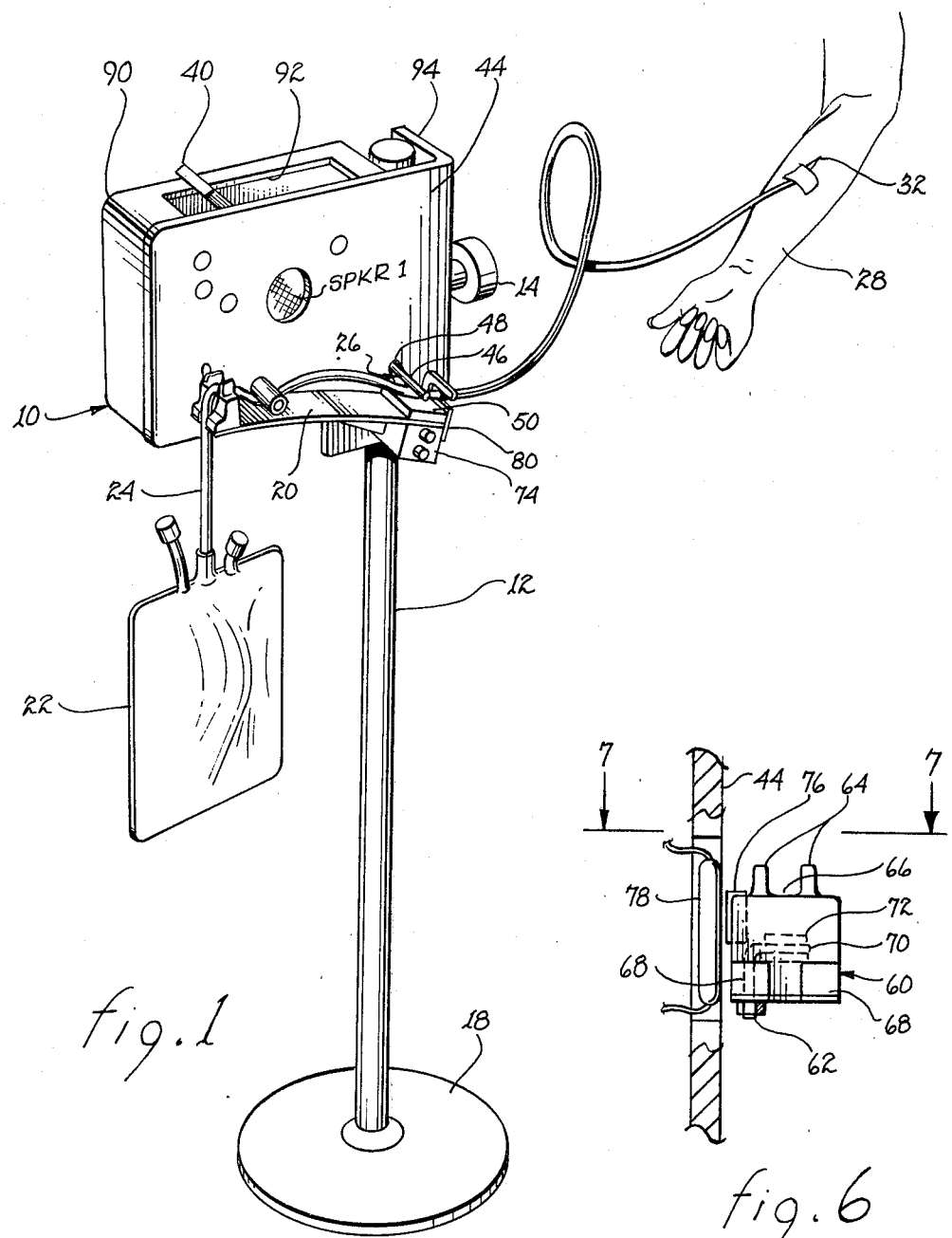
fig. 1
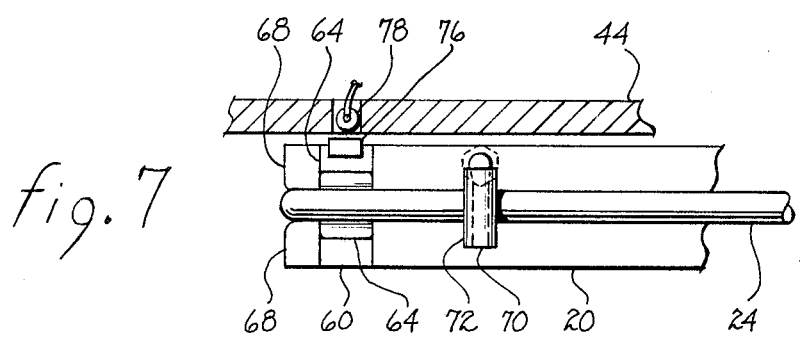
fig. 6
fig. 7

BLOOD COLLECTION BAG WEIGHING DEVICE

The present application is a continuation-in-part application of a copending parent application entitled "BLOOD COLLECTION BAG WEIGHING DEVICE", Ser. No. 81,164, filed Oct. 2, 1979 and assigned to the present assignee.

The present invention relates to weighing devices for blood collection bags and, more particularly, to devices for releasing stored energy by short duration, low energy disruption of a magnetic field.

In private and public blood collection centers, whether for profit, for charity or in affiliation with a hospital, relatively crude techniques are employed to determine the degree of fill of each blood collection bag. In poorly funded blood collection centers, the degree of fill is monitored by one or more operators which results in substantial diversity in the amount of blood in the blood collection bags. Such diversity or nonuniformity may result in penalties or other strictures imposed by a monitoring federal agency for over filled blood collection bags. Where payment by the blood collection center to the blood donors is made on a per blood collection bag basis, overpayment occurs when the blood collection bags are not filled to their norm.

Static weight monitoring apparatus have been employed which provide a visual indication, such as a scale, to an operator upon fill of a blood collection bag commensurate with a norm. Thereafter, further flow is terminated by the operator. Other apparatus which actuate mechanical, electrical or electro mechanical elements on achievement of an approximated weight, have also been developed. One of the more sophisticated apparatus which employs dynamic, rather than static, weighing of the blood collection bag during fill is described in U.S. Pat. No. 4,027,735, which patent is assigned to the present assignee. The apparatus described therein continuously agitates the blood collection bag during fill to obtain good mixing with preservatives predisposed within the blood collection bag while simultaneously weighing the blood collection bag and terminating further flow thereinto on achievement of a predetermined weight.

A prior art device for terminating blood flow into a blood collection bag is described in U.S. Pat. No. 3,960,224. Herein, a pivotally mounted lever is urged into pivotal movement by a spring to squeeze the tubing through which the blood flows. The lever is maintained in a cocked state by an armature of a solenoid through penetrable insertion within a bore in a fixed element and an aperture in the lever. On energization of the solenoid, the armature is retracted from within the aperture in the lever to allow the spring to urge pivotal movement of the lever to squeeze the tubing. A magnetic latch limited to use with cobalt rare earth permanent magnets is described in U.S. Pat. No. 3,671,893; the inventor states therein that such rare earth magnets must be used or else demagnitization will occur upon energization of the coil. Other U.S. patents of some interest include: U.S. Pat. Nos. 2,897,415, 3,283,299, 3,430,230, 3,642,080 and 4,198,626.

The achieve uniformity of fill of blood collection bags and remove a dependency upon an in situ or transportable source of substantial power, the device described hereinafter was developed. This device employs a blood collection bag weight responsive trigger to generate a very low energy electrical signal from a self-contained source of electrical power to release stored energy and perform the work required. Thereby, the device is readily fully self-contained and will accurately monitor and terminate the filling process of blood collection bags.

It is therefore a primary object of the present invention to provide a monitoring device for terminating the flow of blood into a blood collection bag on achievement of a predetermined weight of fill.

Another object of the present invention is to provide a blood collection monitoring device which employs a source of stored energy to terminate on command further flow of blood into a blood collection bag.

Yet another object of the present invention is to provide a low energy triggering mechanism for triggering the release of stored energy to terminate the flow of blood into a blood collection bag.

Still another object of the present invention is to provide a low cost, self-contained device for continuously weighing a blood collection bag during filling thereof and for terminating the filling on achievement of a predetermined weight of the bag.

A further object of the present invention is to provide a low energy consumption triggering mechanism for momentarily and nondestructively disrupting the magnetic field of a barium ferrite permanent magnet, which disruption releases stored energy to perform useful work.

A yet further object of the present invention is to provide a momentarily accuated electrical circuit for momentarily disrupting the field of a barium ferrite permanent magnet to release a magnetically retained element without appreciable impairment of the magnetic properties of the magnet.

A still further object of the present invention is to provide a circuit for disrupting the magnetic field of a permanent magnet and subsequently generating an indication to an operator that disruption has occurred.

A still further object of the present invention is to provide a circuit for disrupting the magnetic field of a permanent magnet to actuate a clamp for terminating blood flow to a collection bag and for providing a first indicium of proper operation and a second indicium of improper operation.

These and other objects of the present invention will become apparent to those skilled in the art as the description thereof proceeds.

The present invention may be described with greater specificity and clarity with reference to the following drawings in which:

FIG. 1 illustrates the blood collection bag weighing device in operation;

FIG. 6 illustrates an end view of the tubing retainer;

FIG. 7 is a top view taken along lines 7—7, as shown in FIG. 6;

Figure 2:
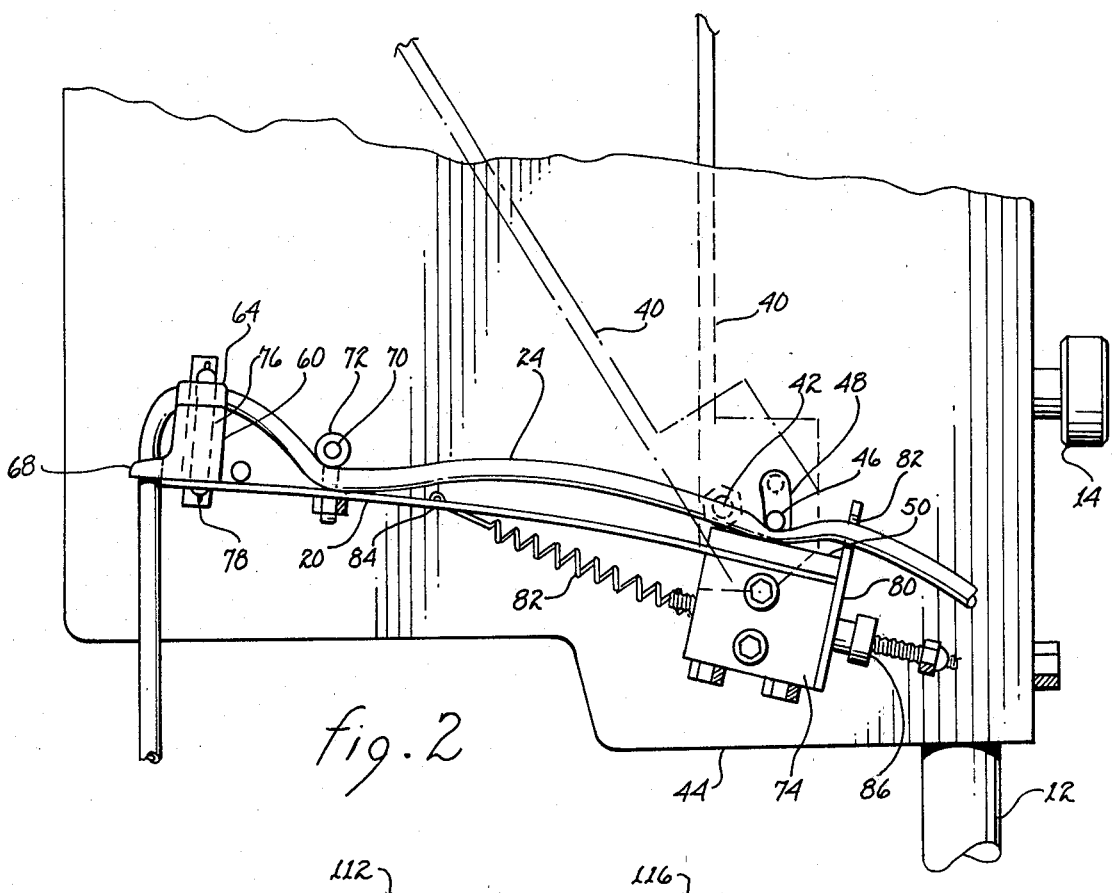
FIG. 2 illustrates the face plate and leaf spring of the device.

Referring to FIG. 1, there is shown a weighing device 10 supported upon a post 12 by retainer means of which knob 14 is shown. The post is anchored to and extends upwardly from a pedestal or platform 18. A leaf spring 20 extends from weighing device 10 to suspendingly support a blood collection bag 22. Fill tube 24 extends from the interior of the blood collection bag via actuatable clamp 26 to an arm 28 of a doner. As is well known, the end of tubing 24 is terminated by a needle 32 inserted into the artery of the donor. To achieve a satisfactory gravity augmented flow rate from the donor to the collection bag, the collection bag should be maintained at a height slightly below that of needle 32.

The structure and operation of clamp 26 will be reviewed with joint reference to FIGS. 1, 2, 3, 4 and 5. The clamp includes a spring loaded member or bar 40 of steel or of other magnetically responsive material, and which bar is pivotally mounted upon bolt 42 extending rearwardly from face plate 44. A rod 46 extends from bar 40 through a curved slot 48 in the face plate and is positionable in proximity with anvil 50 mounted to the front of the face plate. The relationship of these components is such that in the downwardly pivoted position of bar 40, (shown in dashed lines in FIG. 3) rod 46 may lie upon and be supported by anvil 50 to insure that anything disposed intermediate the anvil and the rod will be squeezed by a force equivalent to the spring force exerted by spring 34; which spring extends from a fixed anchor 36 of the face plate to attachment point 38 on rod 40.

The bar is maintained in the cocked or raised position by permanent magnet 52. The magnet is loosely mounted upon bolt 54 by nut 55 to insure continuing alignment conformance between face 56 of the magnet and side 58 of bar 40 and insure maximum magnetic retention force therebetween.

When bar 40 is in the raised position, sufficient space exists intermediate rod 46 and the upper surface of anvil 50 to accommodate tubing 24 therebetween without unduly squeezing the tubing and constricting the flow of blood therethrough. On disengagement between magnet 52 and bar 40, the bar will pivot downwardly about bolt 42 until further downward pivotal movement is constrained by rod 46. Such constraint upon further pivotal movement is presented by tubing 26 and the underlying anvil; see FIG. 2. In the downward pivotal position of bar 40, as illustrated by the dashed lines in FIG. 3, the downward force exerted by rod 46 results in squeezing of tubing 24 and complete restriction of further blood flow therethrough. Thus, further fill of blood bag 22 (see FIG. 1) is constrained by the force of spring 34 acting through rod 46.

It may be noted that the moment arm present between the center of bolt 42 and attachment point 38 through which spring 34 acts varies from a minimum when bar 40 is in the retained state to a maximum when the bar is in the clamped state. Thereby, a first magnitude of force is exerted by the bar when in the retained state and which is less than a second magnitude of force exerted by the bar in the clamped state.

The blood collection bag weight sensing apparatus will be described with primary reference to FIGS. 2, 3, 4, 5, 6 and 7. Blood collection bag 22 is suspended from one end of leaf spring 20 by its own tubing 24. A pedestal 60 is attached to the free end of the leaf spring. The pedestal includes a pair of upwardly extending ears 64 spaced apart from one another to slightly grip tubing 24 disposed therebetween. Surface 66 may be roughened by cross-hatching or the like to increase the friction between the surface and the tubing placed thereon to minimize the possibility of having the tubing slip. A pair of lugs 66 extend from the side of pedestal 60 to serve as guides for and gently grip the tubing depending from ear 64. A guide 70 attached to leaf spring 20 by nut 62 or the like includes a cross arm beneath which tubing 24 is placed to maintain the tubing bearing against surface 66 of the pedestal and thereby increase the frictional contact between the tubing and the pedestal. The cross arm may be enveloped with a sleeve 72 or the like to constrain slippage between the guide and tubing 24. A magnet 76 is attached in proximity to the free end of the leaf spring for cooperation with a magnetically responsive reed switch 78 disposed in the face plate. The other end of the leaf spring is rigidly attached to face plate 44 by mounting 74, which mounting includes anvil 50. A bracket 80 extends upwardly from mounting 74 and includes a slot 82 for receivingly retaining and positionally maintaining tubing 24.

As the blood collection bag is filling, its weight will increase commensurate with the volume of fill. The increasing weight of the blood collection bag will draw the free end of the leaf spring downwardly. Reed switch 76 is positioned within face plate 44 in operative proximity to the location of magnet 76 when the leaf spring is vertically displaced commensurate with the predetermined filled weight of the blood collection bag. Thus, the reed switch will be actuated by the magnet when the blood collection bag is filled to the predetermined weight. A preload spring 82, as particularly shown in FIG. 2, extends between an attachment point 84 of leaf spring 20 and mounting 74. Adjustment mechanism 86 may be incorporated for spring load adjustment to counteract long-term drift of the mechanical components and for periodic calibration. As will be described in further detail below, this actuation of the reed switch is employed to generate a signal to terminate further flow of blood into the blood collection bag.

A coil of wire 88 is disposed in proximity to permanent magnet 52 in such a manner as to cause cancellation or at least disruption of the magnetic field produced by the permanent magnet on electrical energization of the coil. In the embodiment illustrated, the coil is disposed intermediate the two pole pieces of the permanent magnet assembly. Disruption of the magnetic field of magnet 52 will produce a reduced magnetic retention capability of the magnet. Empirically or by engineering analysis, the field strength of the permanent magnet is selected to be sufficient to retain bar 40 thereagainst with a margin of safety. A disruption of the magnetic field sufficient to reduce the magnetic force to a value insufficient to retain the bar will cause release of the bar. It has been learned through experimentation that the magnet may be of the inexpensive barium ferrite type and contrary to general opinion of those skilled in the art, the imposition of the momentary magnetic field disruption will not appreciably impair the magnetic properties of the magnet.

Assuming that the magnetic field disruption produced by the coil is enough to reduce the magnetic retention force below a minimum, bar 40 will be released. As soon as release, that is physical separation between the magnet and bar, is effected, an air gap will develop. The air gap substantially impairs the retention capability of the magnet. By experimentation, it has been learned that a disruption of the magnetic field for approximately one millisecond will result in the development due to the force of spring 34 of an air gap of approximately 0.001 inches. This air gap, even though very minute, combined with the momentum of the pivoting bar, prevents recapture of the bar by the magnet and the bar will continue to pivot about bolt 42. The resulting repositioning of the bar will bring rod 46 to bear against and squeeze tubing 24, as described above.

Figure 3:
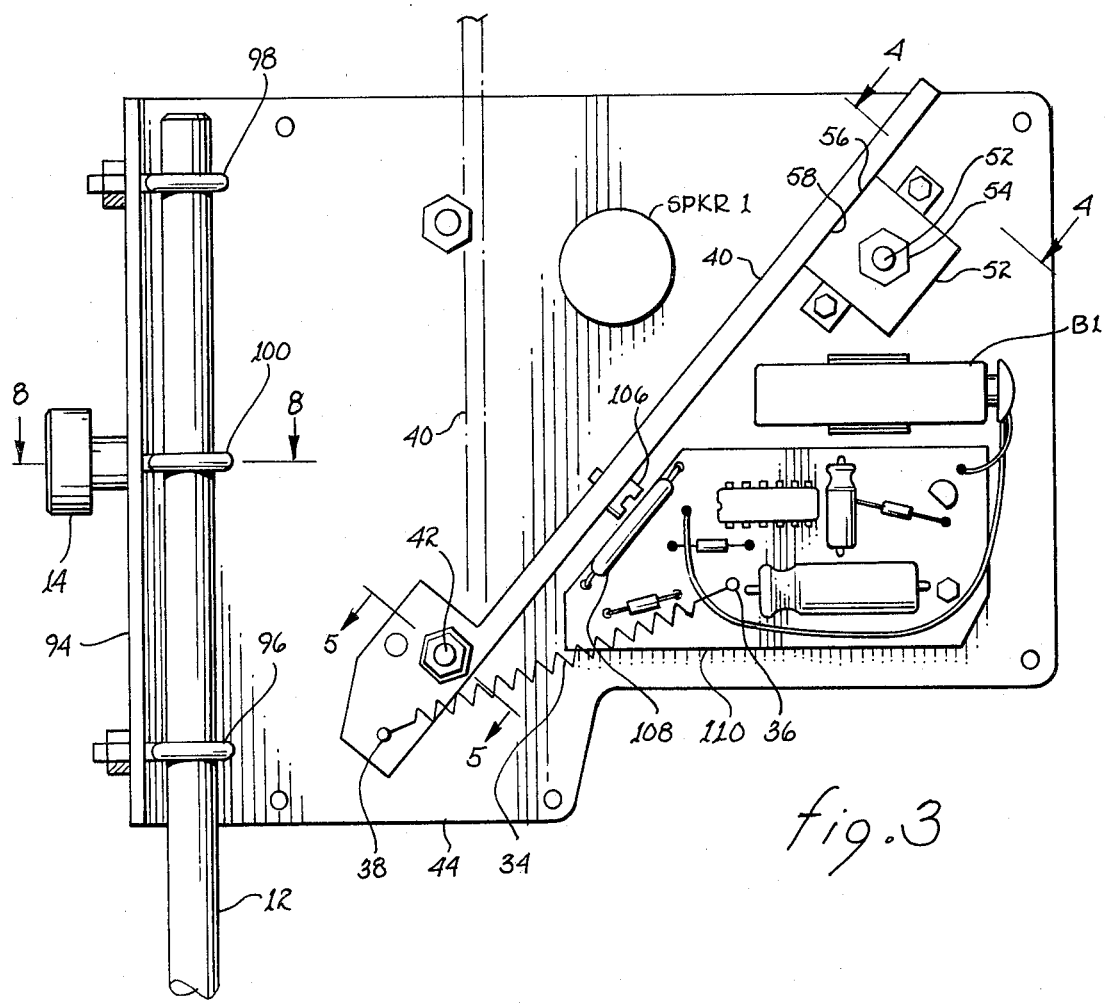
FIG. 3 illustrates the rear of the face plate and components attached thereto.
Figure 5:
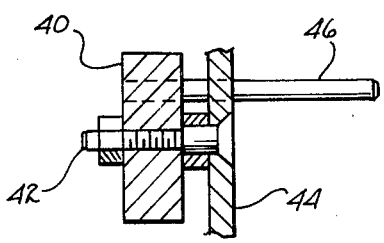
FIG. 5 is a cross-sectional view taken along lines 5—5, as shown in FIG. 3.
Figure 4:
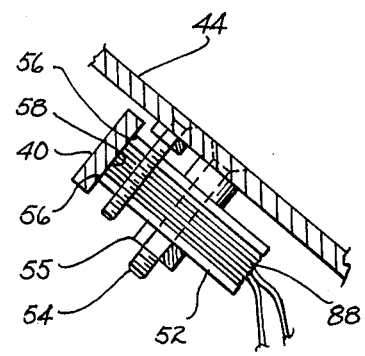
FIG. 4 is a partial cross-sectional view taken along lines 4—4, as shown in FIG. 3.
Figure 8:
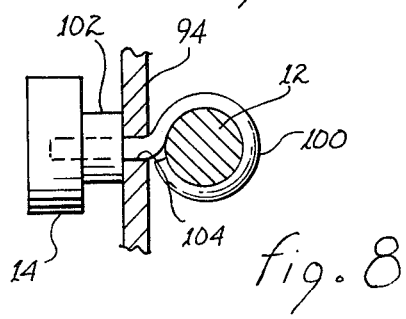
FIG. 8 is a partial cross-sectional view taken along lines 8—8, as shown in FIG. 3.

Referring jointly and primarily to FIGS. 1, 3 and 8, secondary structure attendant weighing device 10 will be described. The device includes a face plate 44, which face plate serves as a mounting for the operative components of the weighing device. A cover 90 is attached to the face plate for shielding and protecting various of the components attached to the rear of the face plate. This cover includes an aperture 92 through which bar 40 extends and within which the bar may be repositioned. The end of cover 90 terminates short of flange 94 extending rearwardly from face plate 44 wherebetween a vertical cavity is defined. Flange 94 supports a pair of eye bolts 96, 98 configured to penetrably receive post 12. A third eye bolt 100 (see FIG. 8) includes a threaded shank 102 extending through an aperture 104 in flange 94. Knob 14 is in threaded engagement with the shank to draw the eye bolt toward the flange and out of alignment with eye bolts 96, 98. Upon penetration of post 12 through the three eye bolts, repositioning of eye bolt 100 by turning knob 14 exerts a lateral force upon the post intermediate eye bolts 96, 98 and substantially increases the frictional contact between the eye bolts and the post. Such frictional contact precludes unwanted displacement of weighing device 10 along the post. Thereby, the height at which the weighing device is positioned along the post is readily and quickly adjustable.

Referring to FIG. 3, there is illustrated a permanent magnet 106 attached to rod 40. A magnetically responsive reed switch 108 is attached to face plate 44 via circuit board 110 or the like. The reed switch is located to be magnetically responsible to magnet 106 when rod 40 is magnetically retained by magnet 52. Thereby, on positioning of rod 40 in the cocked position, reed switch 108 is closed.

Figure 9:
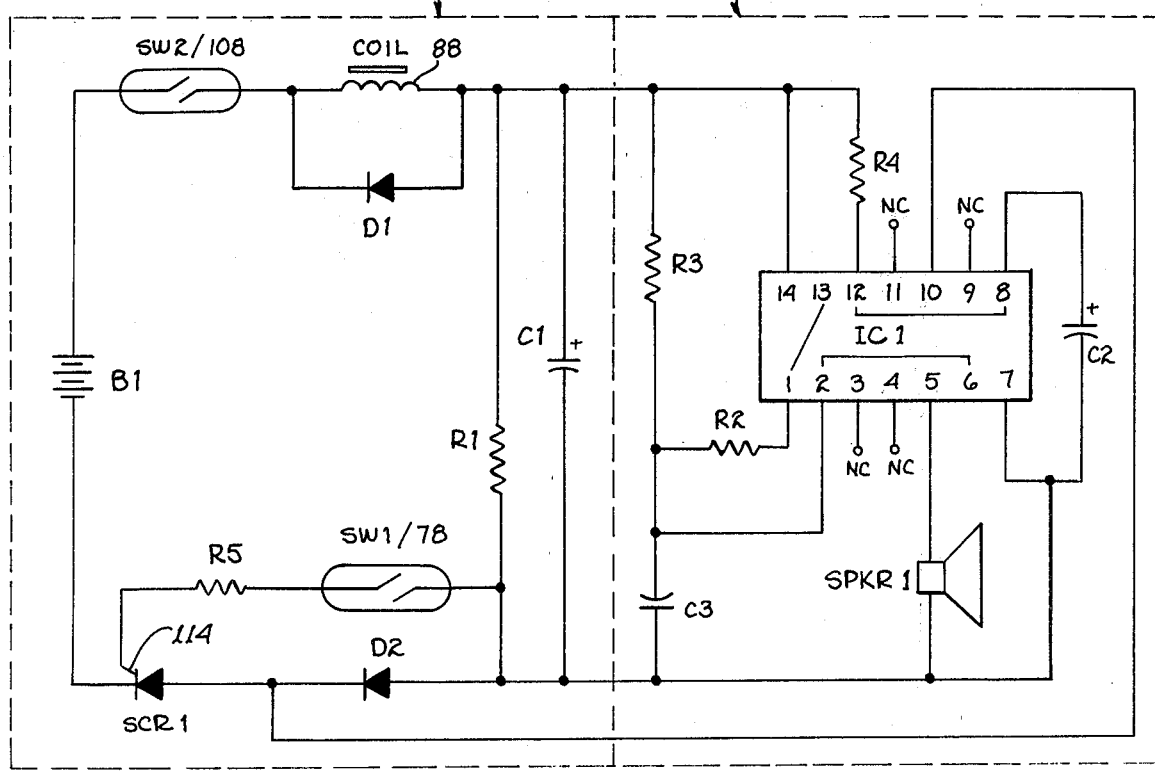
FIG. 9 is a schematic diagram.

Referring to FIG. 9, there is illustrated within block 112 a circuit for generating a short duration low energy pulse for disrupting the magnetic field of magnet 52. When magnet 106 is brought into proximity with reed switch SW2/108 by moving rod 40 to the cocked position, the reed switch will be actuated and close. When reed switch SW1/78 is closed by downward movement of leaf spring 20 bringing magnet 64 into operative engagement therewith, current flows from the positive terminal of battery B1, through switch SW2 (previously closed), through magnetic coil 88, through resistor R1, through reed switch SW1/78, through resistor R5, through gate electrode 114 of silicon controlled rectifier SCR1 to the negative terminal of the battery. The current flow through gate electrode 114 will trigger the silicon controlled rectifier to its "on" state. When the silicon controlled rectifier is in the "on" state, a large current pulse, on the order of 2 to 3 amperes, flow from the positive terminal of battery B1, through switch SW2, through coil 88, through capacitor C1 (as displacement current), through diode D2 and through the silicon controlled rectifier back to the negative terminal of the battery. This current tapers in a few milliseconds and finally ceases as capacitor C1 becomes charged. The silicon controlled rectifier is maintained in the "on" state as current continues to flow through gate electrode 114. The current flow through coil 88 at the time the silicon controlled rectifier switches to the "on" state results in a momentary disruption of the magnetic field of magnet 52. This magnetic field disruption produces a commensurate reduction in rod retaining force of magnet 52 and under the influence of spring 34 (see FIG. 3), pivotal movement of rod 40 is initiated. The resulting air gap between the rod and magnet 52, as described above, is sufficient to prevent a recapture of the rod upon termination of the magnetic field disruption. As rod 40 moves pivotally, magnet 106 is displaced from reed switch 108 and will no longer actuate the reed switch and the latter will open. The current to gate electrode 114 is therefore interrupted and the silicon controlled rectifier will be switched to its "off" state.

The annunciator circuit to provide an operator with indication of the completion of a cycle of operation of weighing device 10 is contained primarily within block 116 shown in FIG. 9. The heart of the annunciator circuit is an integrated circuit IC1 of the "dual timer" type. The annunciator circuit is energized by the current pulse and subsequent thereto by the charge placed upon capacitor C1. The tone producing oscillator circuit is developed by resistor R2, resistor R3, capacitor C3 and one of the "timers" of the integrated circuit. This circuit is normally activated by the circuit composed of resistor R4, capacitor C2 and the second half of the "dual timer" circuit for approximately one second. Thus, termination of the blood flow, or donation, will be signaled by an approximately one second tone emitted from speaker SPKR1.

In the event some obstruction or malfunction prevents rod 40 from pivoting, switch SW2 will not open; accordingly, silicon controlled rectifier SCR1 will remain in the "on" state and a voltage will be present at terminal 10 of the integrated circuit. Energization of the integrated circuit at pin 10 will result in an override of the resistor 4, capacitor C2 circuit and the annunciator oscillator circuit energizing speaker SPKR1 will continue to produce an audible tone. After the operator's attention has been drawn, further emission of the audible tone may be terminated by the operator by repositioning rod 40 and thereby opening reed switch SW2/108.

The following table lists components suitable for use in the above described circuit:

| R1 | Resistor, | 470 Ω | ¼ watt |
|---|---|---|---|
| R2 | Resistor, | 240 KΩ | ¼ watt |
| R3 | Resistor, | 560 KΩ | ¼ watt |
| R4 | Resistor, | 150 KΩ | ¼ watt |
| R5 | Resistor, | 2.2 KΩ | ¼ watt |
| C1 | Capacitor, | 2200 μf 10v | Electrolytic |
| C2 | Capacitor, | 10 μf 10v | Electrolytic |
| C3 | Capacitor, | 910 pf | Ceramic |
| D1 | Diode, | IN4001 | |
| D2 | Diode, | IN4001 | |
| SCR1 | Silicon controlled rectifier, C103YY, (General Electric) | | |
| IC1 | Integrated circuit, | 556 "DUAL TIMER" | |
| SW1 | Reed Switch, | Magnetically actuated | |
| SW2 | Reed Switch, | (SAME) | |
| SPKR1 | Speaker, | Piezo - Electric annunciator, or speaker | |
| B1 | Battery, | 9 volt Alkaline | |

By experimentation, it has been learned that conventional and readily commercially available 9 volt batteries (generally referred to as transistor radio batteries) may be employed. Such a battery is small, lightweight, inexpensive and is readily mountable permanently within housing 90, as illustrated in FIG. 3. The energy capacity of a 9 volt battery of this type is approximately 8,000 joules. The amount of energy consumed per operation is extremely low and a battery may last for a long time and battery replacement is primarily a function of the shelf life of the battery. The added expense of rechargeable batteries is not justified. Accordingly, the operating expenses are extremely low. It may be noted that there exists no need for any other external or internal sources of electrical or mechanical power.

While the above description of the present invention has been primarily couched within the context of a weighing device for blood collection bags, the essential features of the present invention may have use in many totally unrelated fields. That is, the gist of the present invention is that of releasing stored mechanical potential energy maintained by an inexpensive barium ferrite permanent magnet through generation of a short duration low energy magnetic field to disrupt the magnetic field of the permanent magnet without causing appreciable reduction of the magnetic properties of the magnet. Various applications of this principle which come to mind in areas unrelated to the present invention include the following:

(1) the use of a permanent magnet in place of an electromagnet for transporting ferrous materials in junkyards, material handling locations, etc.; the only requirement for electrical power would exist at such time as the retained material were to be released. The difference in quantity of electrocal power consumption between the prior art devices and a device incorporating the present invention is very substantial;

(2) a magnet could be employed to maintain the firing pin of a firearm in the cocked position. The trigger would not have to perform a mechanical release function but could be employed simply to close a circuit to disrupt the magnetic field of the magnet and permit release of the firing pin in response to a cocked spring acting upon the firing pin. By avoiding the mechanical impediments to triggers, flinching, anticipation and other accuracy robbing reflexes are avoided;

(3) traps, fish hooks and similar devices presently relying primarily upon mechanical triggering means and requiring certain forces could be adapted to incorporate the features of the present invention and thereby avoid the mechanical impediments attendant the respective triggering mechanisms;

(4) latching relays, such as bistable relays, having a permanent magnet and a field disruptive coil corresponding with each state and permitting switching from one state to another by selective actuation of one of the coils;

(5) any device wherein it is advantageous to employ extremely low triggering forces to initiate high actuation forces;

(6) any device wherein it is preferable to have a trigering force totally unrelated in magnitude to the value of the force to be released; and (7) any device requiring a high resolution low power trigger or initiation signal to release or actuate a substantial source of potential energy.

In addition to the form of stored energy already discussed, namely mechanical potential energy, there exist other forms of stored energy that may be released to perform useful work by the momentary disruption of the magnetic field of a permanent magnet. For example, mechanical kinetic energy may be stored in the form of the rotating flywheel, the axle of which is supported by a permanent magnet against some bias force, such as gravity. By momentarily disrupting the field of the permanent magnet, the flywheel could be released to move to a new position as a result of the applied bias force. In this new position the fly wheel could rest against a driven wheel and cause the driven wheel to rotate and perform some useful work. As a second example, the stored energy could be electrodynamic energy embodied by charged particles, such as electrons, circulating in a cyclotron in which the magnetic field is produced by permanent magnets. The field of the permanent magnets may be momentarily disrupted to allow the charged particles to escape the circular path to perform some useful work.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

I claim:

1. A blood collection bag weighing device for filling a blood collection bag with a predetermined weight of blood flowing from a tube extending from the vascular system of a donor, said device comprising in combination:

(a) means for clamping the tube, said clamping means including a member for embodying stored energy when positioned in a retained state and for clamping the tube when positioned in a clamped state, said member including a planar surface and means for exerting a first magnitude of force against retention in the retained state and a second magnitude of force for clamping the tube in the clamped state;

(b) a permanent barium ferrite magnet for overcoming the first magnitude of force to magnetically capture and retain said member in the retained state, said magnet including a straight edge and movable mounting means for accommodating realignment of said magnet to position said straight edge of said magnet in aligned contacting relationship with said planar surface of said member and maximize the magnetic coupling therebetween;

(c) means for momentarily disrupting the magnetic field of said magnet to a value insufficient to overcome the first magnitude of force and independent of the magnitude of the second magnitude of force and permit repositioning of said member from the retained state to the clamped state in response to said exerting means;

(d) means for sensing achievement of the predetermined weight by the blood collection bag during the filling of the blood collection bag; and (e) means for generating an electrical signal in response to said sensing means to energize said disrupting means;

whereby, the energy level of said barium ferrite magnet and of said generated electrical signal may be unrelated to the level of energy of the second magnitude of force to clamp the tubing.

2. The device as set forth in claim 1 wherein said generating means includes means for producing a further signal to alert an operator of the state of fill of the blood collection bag.

3. The device as set forth in claim 2 wherein said producing means produces a yet further signal to alert an operator of malfunction in repositioning of said member from the retained state to the clamped state.

4. The device as set forth in claim 1 wherein said magnet comprises a pair of spaced apart plates.

5. The device as set forth in claim 4 wherein said disrupting means comprises an electrical coil disposed intermediate said pair of plates.

6. The device as set forth in claim 4 wherein said member comprises a pivotally mounted bar and a spring interconnecting said member and a fixed point on said device, the magnitude of force exerted upon said member being a function of the moment arm through which said spring acts, which moment arm varies on positioning said member from said retained state to said clamping state thereby the first and second magnitudes of force are defined by a combination of the spring force and respective moment arms.

7. The device as set forth in claim 6 wherein said device includes an anvil for supporting the tube and said member includes a rod for squeezing the tube against said anvil on positioning of said member in the clamped state to preclude further flow through the tube.

8. The device as set forth in claim 6 wherein said moment arm is greater when said member is in the clamped state than when said member is in the retained state for rendering the second magnitude of force substantially greater than the first magnitude of force.

* * * * *